United States Patent [19]

Kron et al.

[11] Patent Number: 4,858,127

[45] Date of Patent: Aug. 15, 1989

[54] APPARATUS AND METHOD FOR MEASURING NATIVE MAMMALIAN BLOOD VISCOSITY

[75] Inventors: Reuben E. Kron, Bryn Mawr; Mitchell Litt, Philadelphia, both of Pa.

[73] Assignee: KDL Technologies, Inc., Philadelphia, Pa.

[21] Appl. No.: 182,176

[22] Filed: Apr. 15, 1988

Related U.S. Application Data

[63] Continuation-in-part of Ser. No. 868,521, May 30, 1986, abandoned.

[51] Int. Cl.⁴ ........................ A61B 5/02; G01N 11/08
[52] U.S. Cl. .................................. 364/413.07; 73/55
[58] Field of Search ...................... 364/413.07; 73/55; 128/637

[56] References Cited

U.S. PATENT DOCUMENTS

| | | | |
|---|---|---|---|
| 3,720,097 | 3/1973 | Kron | 73/55 |
| 3,999,538 | 12/1976 | Philpot, Jr. | 128/637 |
| 4,083,363 | 4/1978 | Philpot, Jr. | 73/55 X |
| 4,165,632 | 8/1979 | Weber et al. | 73/55 |
| 4,519,239 | 5/1985 | Kiesewetter et al. | 73/55 |
| 4,554,821 | 11/1985 | Kieswetter et al. | 73/55 |
| 4,723,442 | 2/1988 | Manning et al. | 73/55 |

*Primary Examiner*—Clark A. Jablon
*Attorney, Agent, or Firm*—Paul & Paul

[57] ABSTRACT

A clinical whole blood viscometer and a method for obtaining instantaneous whole blood viscosity measurements over a wide range of shear rates with a single blood sample is described. A conventionally acquired sample of fresh blood is drawn from a patient and introduced into the viscometer so as to establish viscous flow, the viscosity measurements being taken by remote sensing devices activated by compliant solids or gases in contact with the sample.

10 Claims, 6 Drawing Sheets

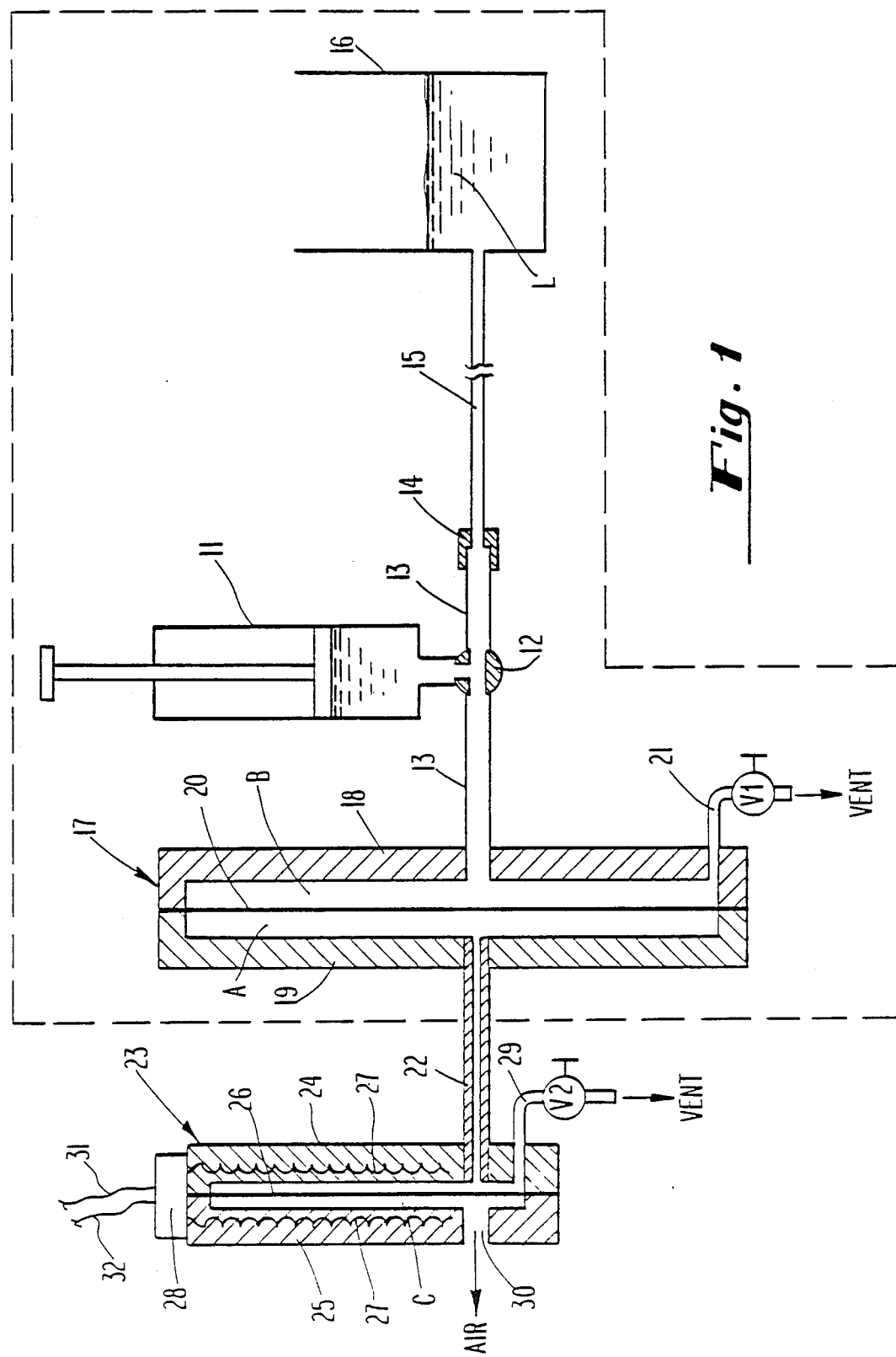

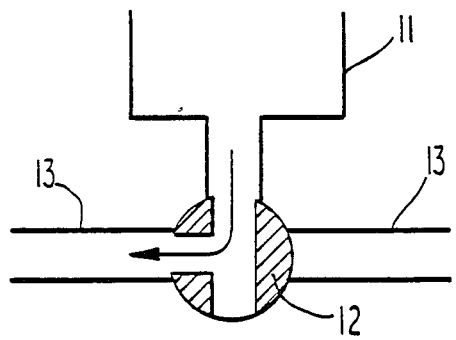
_Fig. 1A_
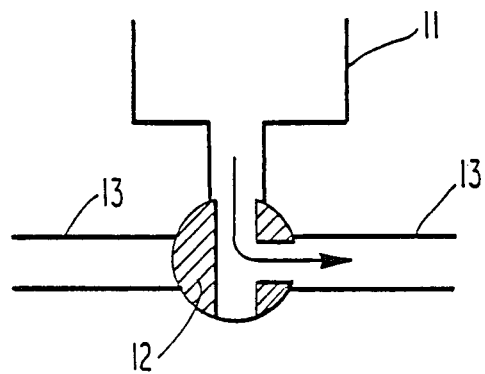
_Fig. 1B_
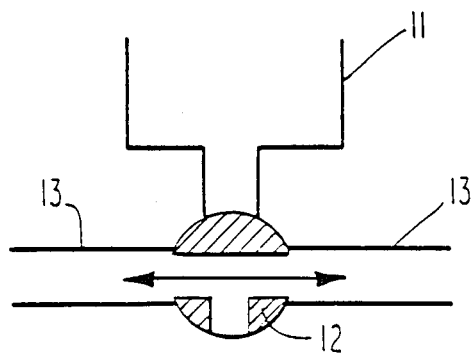
_Fig. 1C_

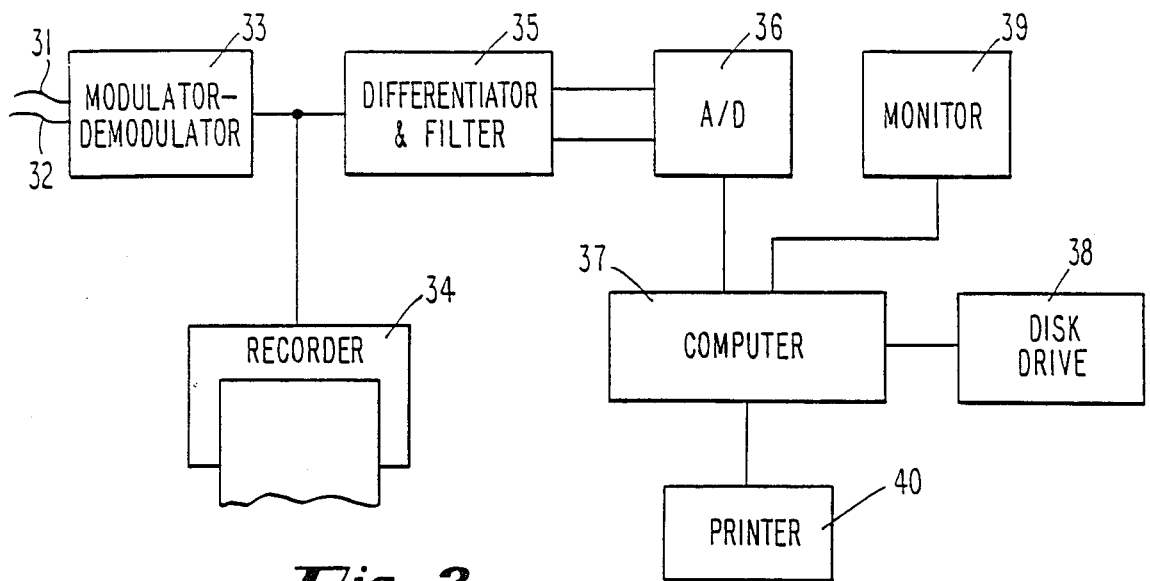
_Fig. 2_
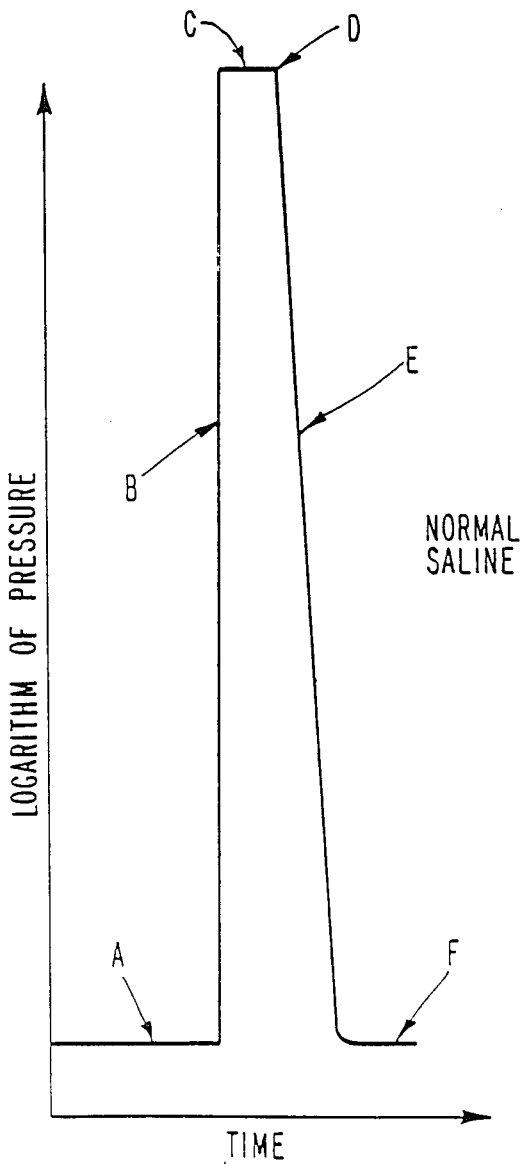
_Fig. 3_

APPARATUS AND METHOD FOR MEASURING NATIVE MAMMALIAN BLOOD VISCOSITY

This invention is a continuation-in-part application of U.S. application Ser. No. 868,521, filed in the U.S. Patent and Trademark Office on May 30, 1986, now abandoned.

FIELD OF THE INVENTION

This invention relates to the measurement of the full range of shear rate dependent viscosities of mammalian blood and of other pseudoplastic fluids, i.e., it generates a profile of viscosity vs. shear rate for non-Newtonian fluids.

DESCRIPTION OF THE PRIOR ART

U.S. Pat. No. 3,720,097 discloses a diagnostic method and apparatus by which a sample of fresh mammalian blood is taken by puncturing a blood vessel and introduced into a system including (1) a capillary generating a linear relationship between pressure and flow of Newtonian fluids, and which is calibrated to deliver 20 ml. of normal saline control solution in one minute at −50 mm. Hg. at 37° C., (2) a programmed vacuum pump which draws the blood sample through the capillary at a variety of pressures in the range of 0 to 200 mm. Hg., (3) an electromagnetic flowmeter which senses the flow rate of the blood through the capillary, and (4) X-Y recording means to instantaneously plot the resultant of the blood flow with respect to pressure variations from which information on the blood viscosity at various shear rates may be determined. U.S. Pat. Nos. 3,999,538 and 4,083,363 disclose methods and apparatus by which a sample of fresh mammalian blood is taken by puncturing a blood vessel while the sample is maintained under a constant predetermined pressure, and the sample is withdrawn through a volume measuring device connected directly to a pressure measuring device. By correlating the time required to withdraw a specified amount of blood with constant pressure maintained during withdrawal, an indication of blood viscosity is obtained. While these methods and apparatus may function as described, their use has been heretofore limited to research projects, and in certain cases the application of the apparatus has necessarily involved the introduction of fresh blood into equipment requiring elaborate cleaning procedures to decontaminate the instrument between experiments. These complexities mitigate against the general, convenient and practical use of this viscometric approach in clinical practice. Later developments to overcome these problems related to U.S. Pat. No. 3,720,097 led to a completely liquid-filled pressure measuring system, in which pressure taps filled with saline solution are used to access the pressure at each end of a capillary containing the blood sample to be measured. The pressure taps are connected to opposite sides of a fluid-filled high compliance differential pressure transducer. After setting up an initial flow in the capillary with a syringe or other external pressure source, the external flow is stopped after the compliant transduce diaphragm has been deflected by an initial amount of differential pressure between the pressure taps. The stored elastic energy of the compliant transducer diaphragm then causes relaxation of the diaphragm and accompanying liquid flow from the high pressure to low pressure side of the transducer with the flow path including the capillary containing the blood as the major resistance to flow. By properly choosing the dimensions and configurations of the elements of the system, the system functions as a first order dynamic system exhibiting an exponential decay and time constant proportional to viscosity for a Newtonian fluid. Viscosity is determined from relationship of shear rate to shear stress. The shear stress is proportional to the pressure in the capillary, while shear rate is calculated from the time rate of pressure change across the capillary, which is proportional to the flow. Moreover, a non-Newtonian fluid will have instantaneous viscosities which vary as a function of the instantaneous shear rates. Therefore, the multiple shear rate dependent viscosities (i.e., the viscosity profile) of fresh blood, a non-Newtonian fluid, can be measured in a single experiment over a 50–100 X shear rate range; also by appropriate choice of capillary and diaphragm the experiment may be designed to last only a short period (typically 20–60 seconds). The shear rate range and experimental duration are selected to provide information of clinical interest (e.g., red cell aggregation effects, particularly at low shear rate) while the overall experimental time is short enough so that any blood sample remains well mixed, and fresh blood samples can be tested without the necessity for anticoagulants. On the other hand, the time for the test is long enough so that very short term relaxation phenomena (less than a few seconds) in the blood do not influence the results. The technique and some of the studies carried out on and results obtained with it are described in the following publications:

A. Downs, A., Litt, M., and Kron, R. E.: Low Shear Rate Viscosity of Fresh Blood, Biorheology, Vol. 17, 25–35, Pergamon Press Ltd., 1980.

B. Yepsen, G., Boutin, D., Litt, M. and Kron, R. E.: Rheological Modelling of Fresh Blood from Transient Pressure Measurements, Biorheology, Vol. 18, 475–484, Pergamon Press Ltd., 1981.

C. Seybert J., Kron, S., Litt, M. and Kron, R. E.: A portable Computerized Clinical Whole Blood Viscometer. Proceedings of the VI International Conference of the Cardiovascular System Dynamics Society, 332–335, November 1984.

Despite the above described improvements of U.S. Pat. No. 3,720,097 there still remain deficiencies which complicate their application in the general clinical setting, including complexity, cost and safety in blood handling, an important factor with the increased risks from blood borne diseases such as AIDS and hepatitis. Moreover, undiluted fresh blood samples cannot easily be recovered from the instrumentation for additional laboratory testing, the system must be disassembled to be cleaned if blood is inadvertently permitted to clot in the fluid-carrying elements and care must be taken to avoid contamination from spilling of blood or blood contact with the operator. Also, because it must be completely liquid filled, the system is sensitive to errors due to the presence of air within any of the fluid enclosures. If anticoagulated (rather than fresh) blood is used, the same deficiencies apply except for the clotting problem, but an additional complication of inhomogeneity due to RBC settling is added. Most importantly, these prior developments are not amenable to the design of a cost effective, disposable device.

With the introduction of FDA-approved drugs to reduce blood viscosity in human beings, the need has arisen for a practical clinical method and apparatus for monitoring hemorheological drug therapy and to determine whole blood viscosity. The method must be inexpensive, safe, easy to use and accurate. Heretofore, "blood viscosity determinants" such as blood hematocrit and fibrinogen content have been used to estimate high shear rate blood viscosity but they suffer from wide individual variability. Also, these indirect determinants are time consuming and expensive to obtain and do not account for many factors such as red blood cell interactions and red blood cell flexibility that contribute heavily to low shear rate blood viscosity. Therefore, accurate, direct, immediate and clinically useful blood viscosity measures cannot be determined in an individual patient from knowledge of hematocrit and fibrinogen parameters alone.

SUMMARY OF THE INVENTION

We have now invented a method and apparatus that provides from a single small sample of blood (or other non-Newtonian liquid) a complete profile of viscosity versus shear rate over the full range of clinical interest in a safe and less complex manner than prior instrumentation and methods. In summary, the method involves acquiring a sample of blood and (1) establishing a body of the sample within a constricted space (such as a capillary), said body in one direction communicating with the atmosphere (or other body of fluid of known pressure), and said body in the other direction communicating either with (a) an enclosed body of blood (or any other liquid) retained by a compliant diaphragm, or (b) with a body of blood having a free surface in contact with a body of air (or other compressible fluid), (2) establishing a body of air of known mass communicating on one side with either (a) the compliant diaphragm or (b) the free surface of said body of blood and on the other side with means for sensing the change in the pressure with time of the known mass of air (3) establishing an initial viscous flow of blood in the constricted space, thereby changing the pressure of the body of air (and deflecting any compliant diaphragm), (4) allowing said compressed body of air (and any deflected compliant diaphragm) to relax, thereby establishing a transient viscous flow in the constricted space, (5) sensing the changing pressure with time in the enclosed body of air during said transient viscous flow with said sensing means, and (6) processing the output of said pressure sensing means to determine the time varying shear stress and shear rate of said sample so as to calculate the changing viscosity of said sample as a function of shear rate during the relaxation of said compliant diaphragm and/or said body of air, thereby providing a continuous profile of viscosity versus shear rate of said sample plus other rheological parameters of interest.

BRIEF DESCRIPTION OF THE DRAWING

FIG. 1 is a schematic diagram of the apparatus of an embodiment of this invention;

FIG. 1A is an enlarged, partial schematic view taken from FIG. 1 and showing syringe 11 and valve 12 filling space B (not shown in FIG. 1A) through conduit 13;

FIG. 1B is an enlarged, partial schematic view, similar to FIG. 1A, showing syringe 11 and valve 12 filling the remainder of conduit 13;

FIG. 1C is an enlarged, partial schematic view, similar to FIG. 1A, showing three-way valve 12 closed off.

FIG. 2 is a schematic diagram of the recording and data analysis instrumentation of an embodiment of this invention;

FIG. 3 is a reproduction of a semi-log record of the viscosity measurements obtained using a sample of normal saline solution in accordance with the process and using the apparatus of an embodiment of this invention;

DESCRIPTION OF THE PREFERRED EMBODIMENTS

Figure 4:
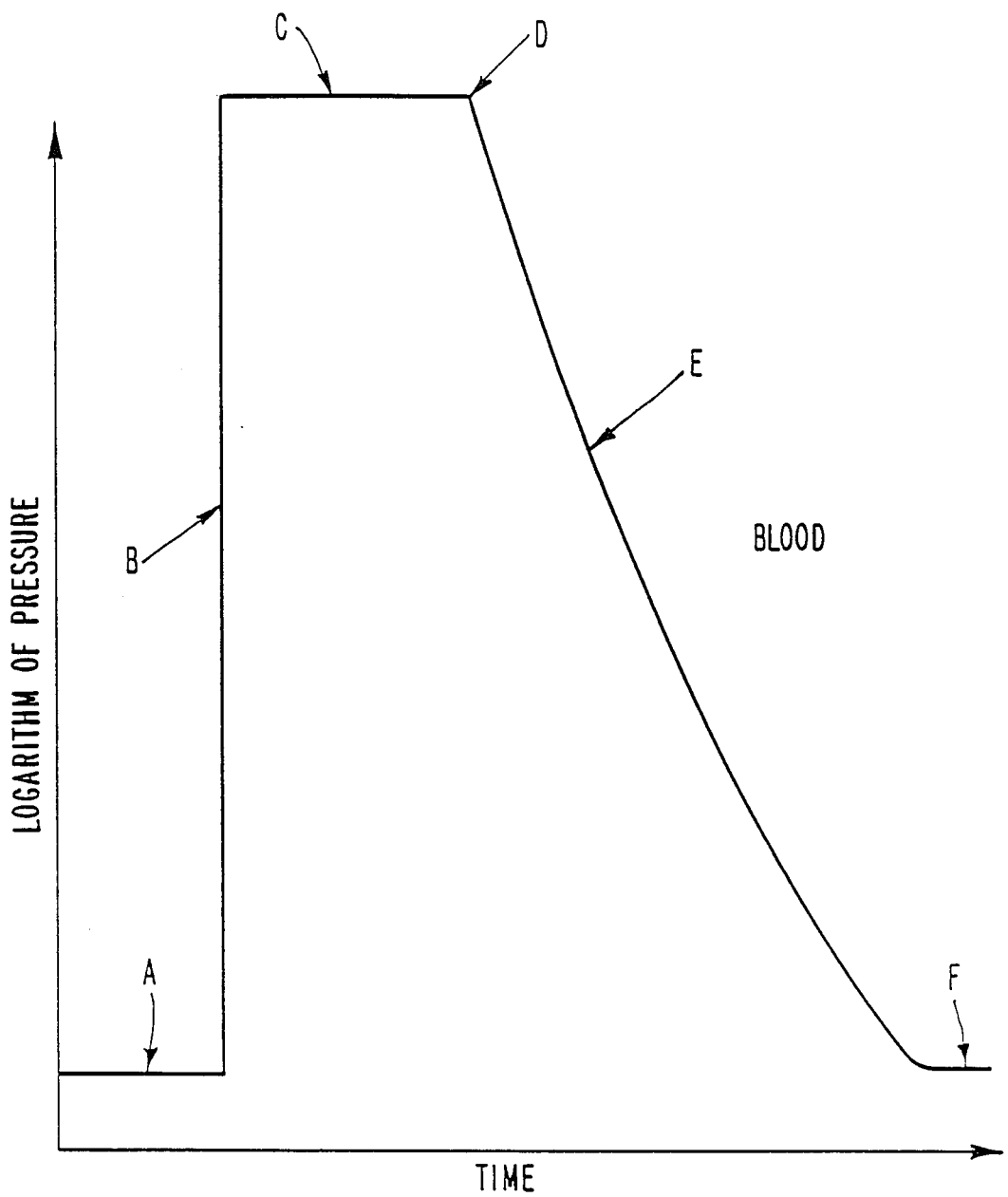
FIG. 4 is a reproduction of a semi-log record of the viscosity measurements obtained using one sample of fresh whole blood in accordance with the process and using the apparatus of an embodiment of this invention.

Referring now to FIG. 1, a conventional hypodermic syringe 11 is shown containing a blood sample. The syringe 11 is adapted for connection to and is shown connected to a three-way valve 12 positioned medially of a conduit 13. One end of the conduit 12 is connected through a connector 14 to a capillary 15, which is in turn connected into an open reservoir 16, shown containing a body of liquid L. The opposite end of the conduit 13 is connected into an assembly 17 consisting of a recessed shell 18, a mating recessed shell 19, a first compliant diaphragm 20 and a venting system to air 21 containing valve V1. As constructed, the first compliant diaphragm 20 is sealed between the recessed shell 18 and the mating recessed shell 19. Moreover, conduit 13 is connected into assembly 17 through recessed shell 18, and a conduit 22 is connected into assembly 17 through mating recessed shell 19 at one end thereof, while at the opposite end it is connected into the measuring assembly 23 consisting of a recessed shell 24, a mating recessed shell 25, a second compliant diaphragm 26, embedded coils 27, coil output means 28, and venting system to air 29 containing valve V2. Mating recessed shell 25 has an opening 30 formed therein open to the air, and the second compliant diaphragm 26 is sealed between recessed shell 24 and mating recessed shell 25.

Referring now to FIGS. 1 and 2, electrical leads 31, 32 connect the coil output means 28 to a transducing modulator-demodulator means 33. The output from the modulator-demodulator 33 is a voltage proportional to the deflection of the compliant diaphragm 26 sensed by coils 27 and is proportional to the pressure of the air or fluid in space A and is fed to a recorder 34 adapted to produce logarithmic pressure versus time curves in semi-log strip chart form, and also to differentiator and filter 35 adapted to produce a voltage proportional to the instantaneous sensed pressure in space A, and a voltage proportional to the instantaneous time rate of pressure change (pressure-time derivative) in space A. These voltages are fed to the inputs of an analog to digital converter 36, which feeds digitized data to a programmed computer 37, which is served by a disk drive 38, a monitor 39, and a printer 40.

In order to carry out the method of this invention, the apparatus is first calibrated with normal saline solution at 37° C. With reference to FIG. 1A, the syringe 11 and three-way valve 12 are used to fill the space B which is the portion of assembly 17 bounded by the first compliant diaphragm 20 and the recessed shell 18, through conduit 13. The venting system 21 is used to eliminate air from space B. Space A consists of the remaining space in assembly 17 bounded by first compliant diaphragm 20 and mating recessed shell 19 and is connected through conduit 22 with the space in pressure measuring assembly 23 bounded by recessed shell 24 and second compliant diaphragm 26. Referring to FIG.

1B, the syringe 11 and three-way valve 12 are now used to fill the remainder of conduit 13 and capillary 15 with normal saline solution. Referring to FIG. 1C, the three-way valve 12 is now set so that there is no flow and no net pressure difference between the portions of the apparatus filled with liquid L because diaphragms 20 and 26 are not deflected and the pressure in space A is atmospheric. Space A is adjusted to atmospheric pressure by means of the venting system 29. At this point, the output voltage of the modulator-demodulator 33 is set at zero to indicate atmospheric pressure throughout the system. The computer is activated with the required program and test settings. The calibration run is begun by introducing more saline solution under pressure from syringe 11 through threeway valve 12 in the position shown in FIG. 1A. This increased pressure causes the first compliant diaphragm 20 to deflect, thereby increasing the air pressure in the space A. In response to this increased air pressure, the second compliant diaphragm deflects against the atmospheric pressure in space C which is between diaphragm 26 and recessed shell 25, and that amount of deflection is sensed by embedded coils 27, generating a signal which is fed through the electrical leads 31, 32 as input to the modulator-demodulator 33. Additional syringe pressure is applied until the voltage output from modulator-demodulator 33 is greater than 10 volts, at which point the recorder 34 and computer 37 are activated. Now the three-way valve 12 is set to close off syringe 11, as shown in FIG. 1C, to permit fluid flow under the force due to the elastic relaxation of both compliant diaphragms and intervening fluid in space A, through conduit 13, capillary 15 and into reservoir 16. As this flow continues, the pressure against first compliant diaphragm 20 decreases with time, as does the pressure in the space A contained by the compliant diaphragms 20, 26, which in turn causes a decreasing voltage signal from modulator-demodulator 33. When this pressure-related signal drops below 10 volts, the computer program is automatically activated so as to acquire data representing the relationship of fluid pressure in space A versus time. At the same time, the recorder 34 continuously prints out a semilogarithmic plot of pressure versus time. FIG. 3 is a reproduction of a print of the resulting viscometric relationships generated by recorder 34 during the calibration of the apparatus with normal saline solution. With reference to FIG. 3, Curve A represents the equilibrium base line pressure before pressure is applied with a syringe. Curve B represents the increase in pressure in space A resulting from compressing the syringe. Curve C is the 10-volt maximum output of modulator-demodulator 33 when pressure is applied with the syringe. While the modulator-demodulator 33 output is above 10 volts, the valve 12 is turned to configuration shown in FIG. 1C and the voltage output decays until it falls below 10 volts as shown at point D. Curve E shown the relaxation and incorporates the pressure-time data required to calculate viscosity. Curve F represents the return of system to baseline atmospheric pressure. The fact that the plot generated for normal saline solution in FIG. 3 (Curve E) is a straight line shows that the system senses saline solution as a Newtonian fluid, whose first order decay in such a system is expected to be negatively exponential, with a single time constant which gives a falling straight line when plotted as a logarithm against time. The fact that the curve is completely linear also shows that no non-linear second order effects are present.

The plotted curve shown in FIG. 4 was generated during a test run utilizing fresh whole blood. After filling the apparatus with normal saline solution as in the aforementioned calibration run, syringe 11 was filled with a sample of fresh whole blood, and by utilizing three-way valve 12, the syringe 11 was operated according to the configuration shown in FIG. 1B so as to displace saline from the portion of conduit 13 between connector 14 and three-way valve 12, through capillary 15 and into the body of liquid L in reservoir 16. At this point, three-way valve 12 was set as in FIG. 1C so as to permit flow in each direction through conduit 13 in order to achieve pressure and flow equalization therein. The valve was then turned to configuration shown in FIG. 1A to deflect the diaphragms 22 and 26 so that output of modulator-demodulator 33 exceeds 10 volts. Valve 12 is then turned to configuration shown in FIG. 1C, allowing pressure in space B to relax as in the aforementioned calibration test run. It is noted from comparing FIGS. 3 and 4 that the time represented by Curve C between pressurization and drop of the pressure generated voltage below 10 volts is significantly longer for blood than for the saline solution because of the greater viscosity of blood. Also, it is apparent that curve E, showing decay of the pressure in FIG. 4, is significantly prolonged for blood compared to saline and is curved concave upward. Such nonlinear behavior is characteristic of a pseudoplastic (non-Newtonian) fluid such as blood, and indicates that the viscosity of the blood sample is increasing as the rate of flow (shear rate) decreases. The computer data from the run generating the curve of FIG. 4 (Table I) showed a shear rate range from $1\ sec^{-1}$ to $46^{-1}$, which covers a significant part of the shear rate range of clinical interest in analyzing blood rheology. Within said range, the viscosity of the blood sample varied from 2.5 centipoise to 46 $sec^{-1}$ to 8.6 centipoise at 1 $sec^{-1}$. The computer also fits a Power Law or Casson rheological equation of state to the viscosity data thereby providing parameters which have clinical utility in characterizing the rheology of blood. For the sample shown in FIG. 4, the value of the Power Law exponent n is 0.68 and the value of the parameter K is 0.085. These values are characteristic of fresh blood having the viscosity profile shown in Table I. In order to maintain physiologically meaningful test conditions, the equipment shown in FIG. 1 was enclosed in an air bath at 37° C. The temperature of the air bath may be set at other values if it is desired to study variation of blood rheology with relation to temperature, as in patients with cryoglobulinemia.

TABLE I

| Computer Output of Viscosities of Blood Sample Shown in FIG. 4 at Selected Shear Rates | |
|---|---|
| Shear Rate ($sec^{-1}$) | Viscosity (centipoise) |
| 1 | 8.56 |
| 10 | 4.11 |
| 19 | 3.34 |
| 28 | 2.96 |
| 37 | 2.70 |
| 46 | 2.52 |

In an alternative embodiment of this invention, the pressure sensing means consisting of elements 23–32 of FIG. 1 and containing the second compliant diaphragm 26 and the modulator-demodulator of FIG. 2 are replaced by any pressure transducing device with associated power supply that generates a suitable electrical signal proportional to the pressure in space A, and which is then processed in the described manner by the remaining system of FIG. 2.

Figure 5:
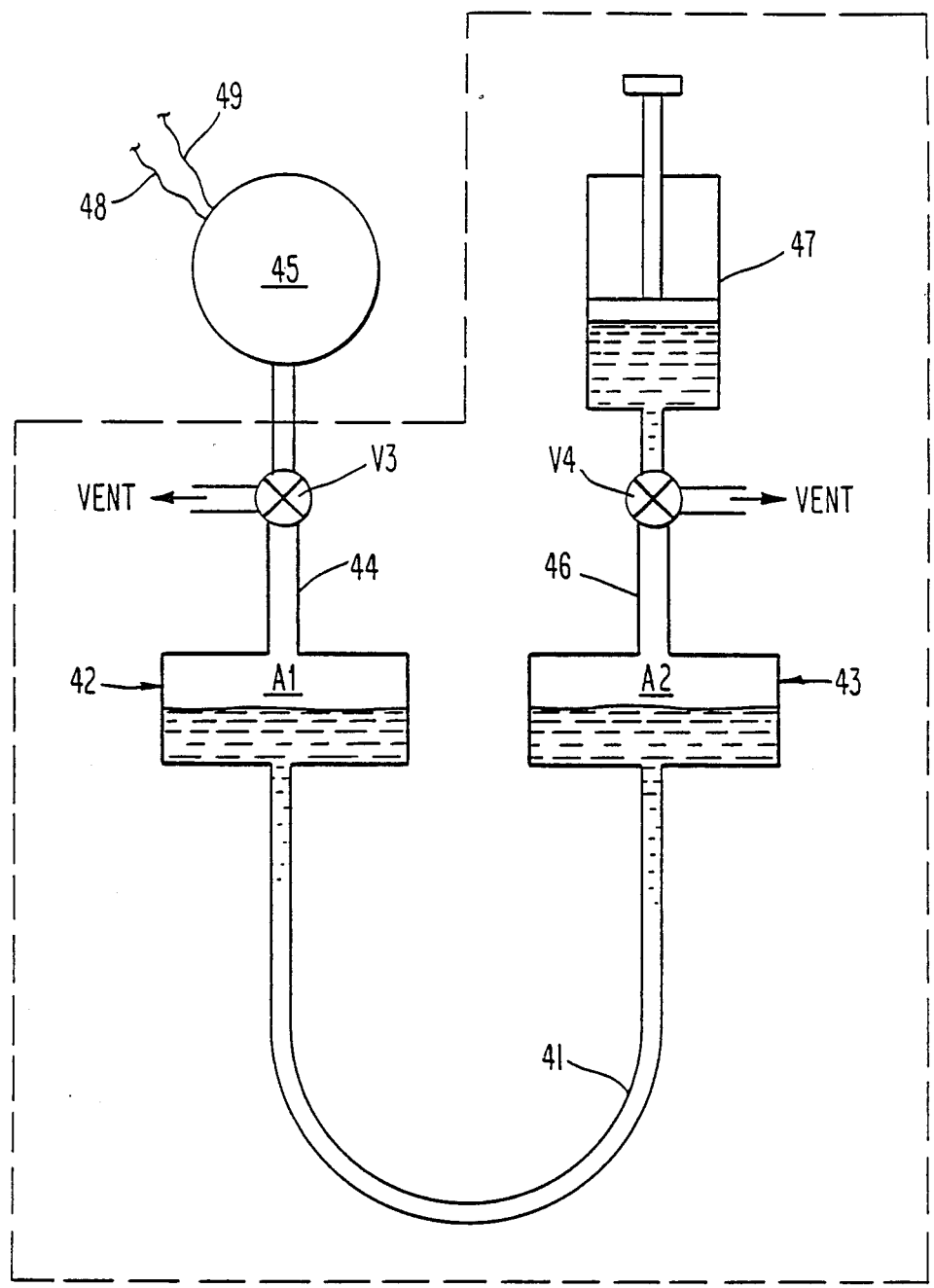
FIG. 5 is a schematic diagram of the apparatus of another embodiment of this invention.

It is not essential to the operation of this invention that the interface between the body of liquid in space B and of air in space A of FIG. 1 be provided by a physical barrier such as compliant diaphragm 20. A suitable configuration can be provided for maintaining the interface between the liquid sample and the air. This is shown in the alternative embodiment of this invention illustrated in FIG. 5. Referring now to FIG. 5, the capillary 41 is connected to two chambers 42 and 43, in which interfaces are provided between the body of liquid and the air in spaces A1 and A2. The chamber 42 is connected through tubing means 44 to the three-way valve V3, which can be vented to the atmosphere or connected to pressure measuring means 45, which communicates to the system of FIG. 2 through wires 48 and 49. Chamber 43 is similarly connected through tubing means 46 to three-way valve V4, which can be vented to the atmosphere or connected to syringe 47.

In order to carry out the method of this embodiment, the system is initially empty of all liquid. Valve V3 is turned to vent the space A1, and valve V4 is turned to connect syringe 47, which contains the test or calibration liquid with tubing 46 and chamber 43. The test liquid is introduced to the system using syringe 47, filling the capillary 41 and partially filling chambers 42 and 43 so as to establish air-liquid interfaces in these chambers. Valve V3 is then turned to connect space A1 with the pressure measuring means 45. At this point the output voltage of the modulator-demodulator 33 of FIG. 2 is set to zero to indicate atmospheric pressure in space A1. The sample syringe 47 is then replaced with an air filled syringe or other pressurization means and pressure applied to chamber 43, the liquid, and the air in space A1. When the pressure output is greater than 10 volts, the valve V4 is turned to vent space A2 to the atmosphere. The higher pressure in space A1 then causes the liquid to flow through capillary 41 from chamber 42 to 43, with reduction in pressure in space A1. Suitable design allows correction for the small changes in pressure head in chambers 42 and 43 during this process. The result is a pressure-time curve comparable to that shown in FIG. 4, which may be processed as described above to determine the viscosity of the test fluid as a function of shear rate. Tests of this embodiment give results comparable to those found with the first embodiment described above.

Figure 6:
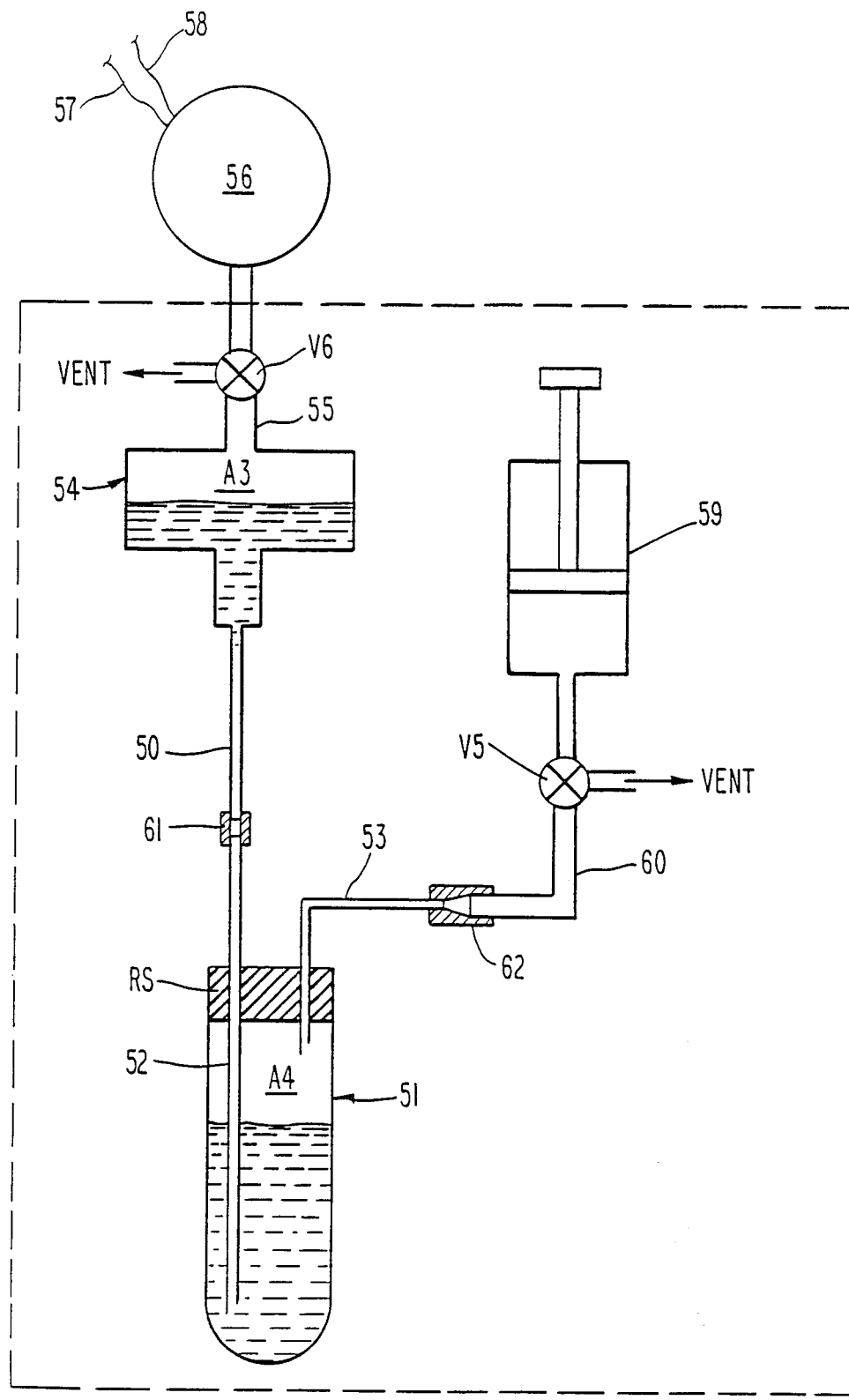
FIG. 6 is a schematic diagram of the apparatus of another embodiment of this invention.

It is also not essential to the operation of this invention that the test fluid be introduced using a syringe. FIG. 6 shows an alternative embodiment of this invention in which the sample of blood or other test fluid is supplied in a standard vacuum-type blood collecting tube. Referring now to FIG. 6, vacuum collecting tube 51 contains the blood sample and is closed by rubber stopper RS. Needle 52, a long hypodermic type needle, is connected using fitting 61 to capillary 50, which in turn is connected to chamber 54. Chamber 54 is connected by tubing means 55 to three-way valve V6, which can either vent air space A3 to atmosphere or connect it to the pressure measuring means 56. Means 56 is connected by wires 57 and 58 to the system shown in FIG. 2. Also, short needle 53 is connected by fitting 62 to tubing means 60, which in turn is connected to three-way valve V5, which can either vent the air space A4 to atmosphere or connect it to air-filled syringe 59.

In order to carry out the method of this embodiment, the apparatus is initially empty of liquid. Stopper RS is pierced by needle 53 whose end extends into air space A4, and needle 52, which extends into the liquid sample to the bottom of tube 51. Value V6 is turned to vent air space A3 to atmosphere. Valve V5 is turned to connect syringe 59 to needle 53 and air space A4. The pressure in air space A4 is then raised using the syringe, pushing liquid from the bottom of tube 51 through needle 52 to fill capillary 50 and partially fill chamber 54 to establish an air-liquid interface in chamber 54. Valve V6 is then turned to close off the vent and connect the pressure measuring means 56 to air space A3. The modulator-demodulator in FIG. 2 is then set to zero to indicate atmospheric pressure in air space A3. Additional pressure on the syringe pressurizes the gas in air space A3 until 10 volts output is obtained for the pressure in air space A3. Valve V is then turned to vent the pressure in air space A4 to atmosphere. The higher pressure in air space A3 then causes the liquid to flow from chamber 54 through the capillary means 50 and needle 52 back into the tube 51, reducing the pressure in air space A3 as a function of time. Suitable design allows for the correction in pressure due to the small height changes in chamber 54 and tube 51. The result is a pressure-time curve comparable to that obtained in the previously described embodiments which can be processed by the system of FIG. 2 to determine viscosity as a function of shear rate and yield results comparable to those found with the previously described embodiments.

In alternative embodiments of this invention, the capillary means described in the embodiments of FIGS. 1, 5 and 6 may be replaced by any fluid resistive device, linear or non-linear, whose flow characteristics are known or may be determined by suitable calibration.

In another embodiment of this invention, the analysis and recording system shown in FIG. 2 may be replaced by any suitable means in which the pressuretime signal resulting from the flow is differentiated by analog or digital means to obtain values proportional to the instantaneous shear stress and shear rate, from which values of viscosity versus shear rate and rheological parameters may be calculated.

It should be evident to anyone familiar with the art of constructing transient flow systems that other embodiments of this invention are possible, in which a time-varying flow of a liquid is used to produce a time-varying pressure in an enclosed air (or other compressible fluid), space such that the viscosity-shear rate characteristics of the liquid can be determined from the dynamic behavior and time constant of the system.

It will also be readily apparent that the method and apparatus of this invention provide an inexpensive, safe, easy to use and accurate determination of fresh whole blood viscosity. Importantly, by this means, blood samples may be tested without introduction into expensive and complex laboratory equipment and the necessity of elaborate cleaning procedures between test experiments. It is apparent that the portions of apparatus of this invention which are enclosed in the dotted lines in FIGS. 1, 5 and 6 are either readily available as disposable items or may be conventionally engineered from disposable materials.

It is also evident that this system is especially applicable to measuring the viscosity of blood because it requires small sample sizes, provides rapid measurement with rapid data reduction, and maximum safety in handling and cleanup since all components that contact the blood may be disposed of. The embodiments of this invention can also be used without adding anticoagulants to the blood sample if desired, since the determination is so rapid. This invention is also applicable to measuring the viscosity-shear rate behavior of non-Newtonian fluids other than blood, but has its greatest advantages when used with biological fluids.

It will also be readily apparent that this invention is applicable to the analysis, diagnosis and treatment of various hematologic disorders such as hyperviscosity syndromes and blood clotting.

This invention also has application to measurements necessary during the production and utilization of polymeric fluid systems in which the time and shear dependent flow properties of the sample are important, such as monitoring the course of polymerization reactions or in quality control of industrial products, such as paints, plastics, pharmaceuticals and foods.

Having thus described our invention, we claim:

1. The method of measuring a continuous profile of viscosity versus shear rate of a sample of blood or other non-Newtonian liquid which comprises the steps of:
   (1) acquiring a sample of blood,
   (2) establishing a body of the sample within a constricted space, said body in one direction communicating with the atmosphere or other body of fluid of known pressure, and said body in the other direction communicating either with (a) an enclosed body of blood or any other liquid retained by a compliant diaphragm, or (b) with a body of blood having a free surface in contact with a body of air or other compressible fluid,
   (3) establishing a body of air of known mass communicating on one side with either (a) the compliant diaphragm or (b) the free surface of said body of blood, and on the other side with means for sensing the change in the pressure with time of the known mass of air,
   (4) establishing an initial viscous flow of blood in the constricted space, thereby changing the pressure of the body of air and deflecting any compliant diaphragm,
   (5) allowing said compressed body of air and any deflected compliant diaphragm to relax, thereby establishing a transient viscous flow in the constricted space,
   (6) sensing the changing pressure with time in the enclosed body of air during said transient viscous flow with said sensing means, and
   (7) processing the output of said pressure sensing means to determine the time varying shear stress and shear rate of said sample and so as to calculate the changing viscosity of said sample as a function of shear rate during the relaxation of either said compliant diaphragm, said body of air, or both said compliant diaphragm and said body of air, thereby providing a continuous profile of viscosity versus shear rate of said sample.

2. The method of claim 1 wherein the constricted space is formed within a capillary.

3. An apparatus for measuring the viscosity profile (shear rate dependent viscosity) of blood or other non-Newtonian liquid comprising in combination (1) capillary or other constricted space means; (2) first conduit means in fluid flow communication with said capillary or constricted space means; (3) three-way valve means positioned medially of said conduit means and adapted to receive the contents of a hypodermic syringe or other source of liquid under pressure; (4) an enclosed assembly comprising a pair of mating recessed shell portions and a first compliant diaphragm sealed therebetween, the distal end of said conduit means communicating into the interior of said assembly through one shell portion; (5) second conduit means communicating at one end thereof into assembly (4) through the mating shell portion thereof; (6) an enclosed measuring assembly comprising a second pair of mating recessed shell portions having a second compliant diaphragm sealed therebetween, the distal end of said second conduit means communicating into the interior of said measuring assembly through one shell portion of said second pair of shell portions, the mating shell portion of said second pair of shell portions having an opening formed therein; (7) coil means embedded within each of said second pair of shell portions adapted to sense the deflection of the said compliant diaphragm; (8) wire means adapted to connect said coils to a modulator-demodulator adapted to generate an output voltage proportional to the deflection of said second compliant diaphragm.

4. An apparatus for measuring the viscosity (shear rate dependent viscosity) of blood or other non-Newtonian liquid comprising in combination (1) capillary or other constricted space means; (2) first conduit means in fluid flow communication with said capillary or constricted space means (3) three-way valve means positioned medially of said conduit means and adapted to receive the contents of a hypodermic syringe or other source of liquid under pressure; (4) an enclosed assembly comprising a pair of mating recessed shell portions and a first compliant diaphragm sealed therebetween, the distal end of said conduit means communicating into the interior of said assembly through one shell portion; (5) second conduit means communicating at one end thereof into the assembly (4) through the mating shell portion thereof; (6) an enclosed pressure measuring assembly comprising pressure transducer means adapted to produce a voltage output proportional to the fluid pressure in the second conduit means; (7) wire means adapted to connect said pressure transducer means to a power unit means adapted to generate an output voltage proportional to the input pressure.

5. An apparatus for measuring the viscosity of blood or other non-Newtonian liquid comprising in combination: (1) capillary or other constricted space means; (2) first chamber means in fluid communication with said capillary or constricted space means; (3) first three-way valve means adapted to connect said chamber means with pressure measuring means or with the atmosphere or other body of fluid of known pressure; (4) second chamber means in fluid communication with said capillary or constricted space means; (5) second three-way valve means positioned to connect second chamber means alternatively to either receive the contents of a hypodermic syringe or other source of liquid under pressure, or connect said second chamber means to atmosphere or other body of fluid at known pressure; (6) pressure measuring means adapted to produce a voltage output proportional to the fluid pressure within the air space of the first chamber means; (7) wire means adapted to connect such pressure transducer means to a power unit adapted to generate an output voltage proportional to the input pressure.

6. An apparatus for measuring the viscosity of a sample of blood or other non-Newtonian liquid comprising in combination (1) capillary or other constricted space means (2) chamber means communicating with the capillary means, (3) pressure measuring means adapted to produce a voltage output proportional to pressure within the air space of said chamber means, (4) first three-way valve means communicating with said chamber means and adapted to alternatively connect said chamber means to said pressure measuring means or to atmosphere or other body of fluid of known pressure, (5) a vacuum-type blood collecting tube sealed by a rubber stopper, (6) long needle means communicating with said capillary means and adapted to pierce the stopper of said collecting tube so as to extend to the bottom of the tube, (7) pressure generating means, (8) short needle means adapted to pierce the stopper of said collecting tube so as to extend only above the normal liquid surface thereof, (9) a second three-way valve means adapted to alternatively connect the blood collecting tube through the short needle means to either an air filled hypodermic syringe, other pressure generating means or to atmosphere or other body of fluid of known pressure, and (10) wire means adapted to connect said pressure measuring means to a power unit adapted to generate air output voltage proportional to the measured input pressure.

7. The apparatus of claims 3, 4, 5 or 6 further including (1) input means adapted to receive the output of said modulator-demodulator means or the combination of said pressure and power unit means; (2) differentiating and filtering means adapted to generate one output voltage proportional to the voltage received by said input means, and another output voltage proportional to the time derivative of the voltage received by said input means; (3) an analog to digital converter adapted to convert the output voltage of said differentiating and filtering means to digital outputs; (4) a computer adapted to receive the digital output of said analog to digital converter; and (5) a program for converting the digital inputs to the computer to values of viscosity versus shear rate, and for computing parameters of rheological equations of state.

8. The apparatus of claims 3, 4, 5 or 6 further including (1) input means adapted to receive the output of said modulator-demodulator means or the combination pressure and power unit means; (2) an analog to digital converter means adapted to convert said input voltage to digital output; (3) a computer adapted to receive the digital output of said analog to digital converter; and (4) a program to differentiate the digitized signal and convert the original and differentiated digital signals to values of viscosity versus shear rate, and for computing parameters of rheological equations of state.

9. The apparatus of claim 7 including in combination a recorder adapted to print continuous logarithmic curves of pressure versus time in strip chart form utilizing the output voltage of said modulator-demodulator or pressure power unit means as input.

10. The apparatus of claim 8 including in combination a recorder adapted to print continuous logarithmic curves of pressure versus time in strip chart form utilizing the output voltage of said modulator-demodulator or pressure power unit means as input.

* * * * *

UNITED STATES PATENT AND TRADEMARK OFFICE
CERTIFICATE OF CORRECTION

PATENT NO. : 4,858,127
DATED : August 15, 1989
INVENTOR(S) : Reuben E. Kron and Mitchell Litt It is certified that error appears in the above-identified patent and that said Letters Patent is hereby corrected as shown below:

Col. 7, line 63, Also  should be --Also--

Col. 8, line 3, "Value V6" should be --Valve V6--

Col. 8, line 16, "Valve V" should be --Valve V5--

Signed and Sealed this

Twenty-fifth Day of December, 1990

Attest:

HARRY F. MANBECK, JR.

*Attesting Officer*   *Commissioner of Patents and Trademarks*